United States Patent [19]

Blaine

[11] Patent Number: 4,652,549

[45] Date of Patent: Mar. 24, 1987

[54] CARDIAC ANTI-HYPERTROPHIC AGENTS

[75] Inventor: Edward H. Blaine, Chalfont, Pa.

[73] Assignee: Merck & Co., Inc., Rahway, N.J.

[21] Appl. No.: 693,066

[22] Filed: Jan. 22, 1985

[51] Int. Cl.$^4$ ............................................. A61K 37/02
[52] U.S. Cl. ........................................ 514/13; 514/12
[58] Field of Search .................................... 514/12, 13

[56] References Cited

U.S. PATENT DOCUMENTS 4,496,544 1/1985 Needleman ................. 260/112.5 R

OTHER PUBLICATIONS

Seidah et al., *Proc. Natl. Acad. Sci., U.S.A.*, 81, 2640 (1984).
Chartier et al., *Biochem. Biophys. Res. Comm.*, 122(1), 171–4 (1984).
Kangawa et al., *Biochem. Biophy. Res. Communications*, 118(1), 131–139 (1984).
Currie et al., *Science*, 221, 71–73 (1983).
Guttmann, *Calcitonin 1980*, Proceedings of International Sym. Milan, Oct. 15–17 (1980).
Rittet et al., *Experientia*, 32(2), 246 (1976).
Chemical Abstracts, 102, 132 (1985), Abst. No. 198634(a).

*Primary Examiner*—Delbert R. Phillips
*Attorney, Agent, or Firm*—Donald J. Perrella; Hesna J. Pfeiffer

[57] ABSTRACT

ANF and peptide subunits thereof and compounds having ANF-like activity have been found to reduce and reverse cardiac hypertrophy.

8 Claims, No Drawings

CARDIAC ANTI-HYPERTROPHIC AGENTS

BACKGROUND OF THE INVENTION

It has been postulated for many years that mammalian cardiac atria serve as sensors that are important in detecting changes in extracellular fluid volume (Gauer et al., Physiol, Rev. 43:423, 1963). Such a receptor function for the cardiac atria is known in the case of vasopressin, the hypothalmic hormone important in regulating the osmotic concentration of the body fluids.

The postulated existence of a substance which would enhance urinary sodium excretion, and hence be involved in regulation of extracellular fluid volume, was demonstrated recently. de Bold et al., Life Sci. 28:89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221:71, 1983). Such action implies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor or ANF but has been referred to also as cardionatrin (de Bold et al., Life Sci. 33:297–302, 1983), atriopeptin (Currie et al., Science 223:67, 1984) and auriculin (Atlas et al., Nature 309:717–719, 1984). Atrial natriuretic factor was shown to be a family of peptides all of which have a common amino acid sequence but differ in length by the presence or absence of 1–8 amino acids on the amino or carboxyl termini.

OBJECTS OF THE INVENTION

It is an object of the present invention to provide cardiac anti-hypertrophic agents. Another object is to provide ANF peptides having cardiac anti-hypertrophic activity. A further object is to provide compositions suitable for physiological administration to a mammaliam species containing biologically active peptide fragments of ANF. These and other objects of the present invention will be apparent from the following description.

SUMMARY OF THE INVENTION

ANF and peptide subunits thereof and compounds having ANF-like activity have been found to reduce and reverse cardiac hypertrophy in mammalian species.

DETAILED DESCRIPTION

The ANF peptides of the present invention may be prepared from their constituent amino acids by standard methods of protein synthesis, e.g., Schroeder et al., "The Peptides", Vol. I, Academic Press, 1965, or Bodanszky et al., "Peptide Synthesis", Interscience Publishers 1966, or McOmie (ed.), "Protective Groups in Organic Chemistry", Plenum Press 1973, the disclosures of which are hereby incorporated by reference.

The peptides of the present invention also may be prepared by recombinant DNA techniques by, for example, the isolation or preparation of appropriate DNA sequences and incorporation of these sequences into vectors followed by insertion of the vectors in a suitable host and expression of the desired peptide therefrom. The use of recombinant DNA techniques is described in many published articles, for example, Maniatis et al., Molecular Cloning, A Laboratory Manual, Cold Spring Harbor, N.Y. 1982, the disclosure of which is hereby incorporated by reference.

Suitable hosts for expression of the ANF peptides include prokaryotic organisms such as *E. coli* and *B. subtilis*, and eukaryotic organisms such as *Saccharomyces cerevisiae* and Chinese hamster ovary cells. It is also to be understood that these proteins can be expressed directly in a mammalian species by means of appropriate expression vectors such as vaccinia, varicella zoster, adeno or herpes simplex viruses.

Specific peptides that fall within the scope of the present invention are the following: A-Cys-Phe-Gly-Gly-Arg-X-Asp-Arg-Ile-Gly-Ala-Glu-Ser-Gly-Leu-Gly-Cys-Asn-Ser-B wherein X is Ile or Met, A is

```
                                                    Ser—
                                                Ser—Ser—
                                            Arg—Ser—Ser—
                                        Arg—Arg—Ser—Ser—
                                    Leu—Arg—Arg—Ser—Ser—
                                Ser—Leu—Arg—Arg—Ser—Ser—
                            Arg—Ser—Leu—Arg—Arg—Ser—Ser—
                        Pro—Arg—Ser—Leu—Arg—Arg—Ser—Ser—
                    Gly—Pro—Arg—Ser—Leu—Arg—Arg—Ser—Ser—
                Ala—Gly—Pro—Arg—Ser—Leu—Arg—Arg—Ser—Ser— or
            Leu—Ala—Gly—Pro—Arg—Ser—Leu—Arg—Arg—Ser—Ser—
``` and B is

-Phe,

-Phe-Arg,

-Phe-Arg-Tyr,

-Phe-Arg-Tyr-Arg or

-Phe-Arg-Tyr-Arg-Arg, wherein the C-terminal group may be a carboxyl group or the amide thereof and wherein the Tyr residue may be iodinated or non-iodinated. These peptides may be either linear or cyclized by means of covalent, e.g., disulfide, bonds between the two cysteine residues. The iodinated derivative is prepared by treating the noniodinated peptide, in a medium containing sodium phosphate buffer, sodium iodide, with chloramine-T (N-chloro-4-methylbenzenesulfonamide sodium salt). The iodination is quenched by addition of sodium thiosulfate and the iodinated peptide isolated by a high performance liquid chromatography (HPLC) column. The radioactively iodinated peptide is prepared similarly using $I^{125}$.

The iodinated derivative is active per se and also is useful as a reference standard in synthesis of the noniodinated synthetic peptides while the radioactively iodinated peptide is useful in in vitro and clinical metabolic half-life studies of the peptides of the present invention. The iodinated derivative has substantially the same biological activity as the non-iodinated peptide.

It is to be understood that the method of treating cardiac hypertrophy according to the present invention is not limited to the specific peptides mentioned above, but is intended to include homologues, analogues, and synthetic derivatives having activity similar to the specific peptides mentioned above.

The peptides of the present invention are useful individually or in combination to treat disorders of electrolyte balance and/or altered vascular resistance in mammalian species, e.g., hamsters, mice and rats, in amount of from about 10 to about 2000 picomoles/kg/min., preferably from about 100 to about 1000 picomoles/kg/min. The peptides may be administered by intravenous infusion, for example in a suitable physiologically acceptable carrier, e.g., saline or phosphate buffered saline.

The following examples illustrate the present invention without, however, limiting the same thereto. The disclosure of each reference mentioned in the following examples is hereby incorporated by reference.

EXAMPLE 1

The peptide Ser-Ser-Cys-Phe-Gly-Gly-Arg-Ile-Asp-Arg-Ile-Gly-Ala-Gln-Ser-Gly-Leu-Gly-Cys-Asn-Ser is prepared as described by Currie et al., Science, Jan. 6, 1984, pp. 67–69.

EXAMPLE 2

The peptide Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg is prepared as described by Currie et al., op. cit.

EXAMPLE 3

The peptide Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg is prepared as described by Atlas et al., Nature 309:717–719, June 21, 1984.

EXAMPLE 4

The peptide Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr is prepared as described by Misono et al., Biochem. Biophys. Res. Commun. 119:524–529, Mar. 15, 1984.

EXAMPLE 5

The peptide Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr is prepared as described by Seidah et al., Proc. Natl. Acad. Sci. USA 81:2640–2644, 1984.

EXAMPLE 6

The peptide Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr is prepared as described by Flynn et al., Biochem. Biophys. Res. Commun. 117:859–865.

EXAMPLE 7

The peptide Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr is prepared as described by Kangawa et al., Biochem. Biophys. Res. Commun. 118:131–139, Jan. 13, 1984.

EXAMPLE 8

The peptide Gly-Pro-Arg-Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr is prepared as described by Seidah et al., op. cit.

EXAMPLE 9

The peptide Ala-Gly-Pro-Arg-Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr is prepared as described by Seidah et al., op. cit.

EXAMPLE 10

The peptide Leu-Ala-Gly-Pro-Arg-Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr is prepared as described by Seidah et al., op. cit.

EXAMPLE 11

The following data shows the effects of a 7-day continuous infusion of a representative peptide of the present invention, namely the peptide of Example 5, at a dosage level of 30 pmole per kg per minute in reversing cardiac hypertrophy.

Heart Weight (grams H$_2$O per 100 grams tissue)

| TREATMENT | |
|---|---|
| SALINE | 0.82 + 0.03 |
| | n = 24 |
| PEPTIDE OF EXAMPLE 5 | |
| | 0.70 + 0.03* |
| | n = 23 |
| NORMAL | |
| TREATMENT | |
| SALINE | 0.53 + 0.03 |
| | n = 17 |
| PEPTIDE OF EXAMPLE 5 | |
| | 0.45 + 0.02 |
| | n = 22 |

*Statistically significant at p value less than 0.05.

The foregoing data illustrate the efficacy of a typical peptide of the present invention for reducing cardiac hypertrophy.

What is claimed is:

1. A method of treating cardiac hypertrophy in a mammalian species which comprises administering an anti-cardiac hypertrophy effective amount of a peptide having the amino acid sequence A-Cys-Phe-Gly-Gly-Arg-X-Asp-Arg-Ile-Gly-Ala-Glu-Ser-Gly-Leu-Gly-Cys-Asn-Ser-B wherein X is Ile or Met, A is Ser—
Ser—Ser—
Arg—Ser—Ser—
Arg—Arg—Ser—Ser—
Leu—Arg—Arg—Ser—Ser—
Ser—Leu—Arg—Arg—Ser—Ser—
Arg—Ser—Leu—Arg—Arg—Ser—Ser—
Pro—Arg—Ser—Leu—Arg—Arg—Ser—Ser—
Gly—Pro—Arg—Ser—Leu—Arg—Arg—Ser—Ser—
Ala—Gly—Pro—Arg—Ser—Leu—Arg—Arg—Ser—Ser— or
Leu—Ala—Gly—Pro—Arg—Ser—Leu—Arg—Arg—Ser—Ser— and B is

-Phe,

-Phe-Arg,

-Phe-Arg-Tyr,

-Phe-Arg-Tyr-Arg or

-Phe-Arg-Tyr-Arg-Arg, wherein the C-terminal group is a carboxyl group or the amide thereof and wherein the Tyr residue is iodinated or non-iodinated and wherein the peptide is linear or cyclized by means of convalent bonds between two cysteine residues.

2. A method according to claim 1 wherein the effective amount is from about 10 to about 2000 picomoles/kg/minute.

3. A method according to claim 1 wherein the peptide is administered in an amount by infusion.

4. A method according to claim 1 wherein the peptide is administered with a physiologically acceptable carrier.

5. A method according to claim 4 wherein the carrier comprises saline or phosphate buffered saline.

6. A method according to claim 1 wherein the peptide is linear.

7. A method according to claim 1 wherein the peptide, is cyclized.

8. A method according to claim 7 wherein the peptide is cyclized by means of disulfide bonds.

* * * * *